US008137680B2

(12) United States Patent
Bardotti et al.

(10) Patent No.: US 8,137,680 B2
(45) Date of Patent: Mar. 20, 2012

(54) ANALYSIS OF SACCHARIDE VACCINES WITHOUT INTERFERENCE

(75) Inventors: Angela Bardotti, Siena (IT); Daniela Proietti, Narni (IT); Stefano Ricci, Siena (IT)

(73) Assignee: Novartis Vaccines and Diagnostics SRL, Siena (IT)

( * ) Notice: Subject to any disclaimer, the term of this patent is extended or adjusted under 35 U.S.C. 154(b) by 894 days.

(21) Appl. No.: 10/593,005

(22) PCT Filed: Mar. 17, 2005

(86) PCT No.: PCT/IB2005/000987
§ 371 (c)(1),
(2), (4) Date: Jul. 29, 2008

(87) PCT Pub. No.: WO2005/090986
PCT Pub. Date: Sep. 29, 2005

(65) Prior Publication Data
US 2008/0286300 A1    Nov. 20, 2008

(51) Int. Cl.
*A61K 39/095* (2006.01)
*G01N 31/00* (2006.01)
*G01N 31/02* (2006.01)
*G01N 21/00* (2006.01)
*G01N 30/02* (2006.01)
*G01J 3/42* (2006.01)

(52) U.S. Cl. ....... 424/250.1; 702/22; 436/161; 436/164; 422/70; 356/319; 356/326

(58) Field of Classification Search .................. None
See application file for complete search history.

(56) References Cited

U.S. PATENT DOCUMENTS
7,117,336 B2   10/2006   Mimatsu et al.

FOREIGN PATENT DOCUMENTS
| EP | 0 462 794 A | 12/1991 |
| WO | WO 02/058737 | 8/2002 |
| WO | WO 03/007985 | 1/2003 |
| WO | WO 2004/103400 | 12/2004 |

OTHER PUBLICATIONS

Ho et al Vaccine 19 (2001) 716-725.*
Claus et al. Mol Gen Genet (1997) 257:28-34.*
Jantzen, E. et al, "Cellular monosaccharide patterns of Neisseriaceae," Acta. Path. Microbiol. Scand. Sect. B, 84 (4): 177-188 (1976).
Bhattacharjee, A. et al, "Structural determination of the poly saccharide antigens of Neisseria-meningitidis serogroup . . . " Canadian Journal of Biochemistry 54 (1): 1-8 (1976).
Bardotti, A. et al, "Quantitative determination of saccharide in Haemophilus influenzae type b glycoconjugate vaccines, alone and in . . . " Vaccine, 18 (19): 1982-1993 (2000).
Bryn, K. et al, "Gas chromatographic screening of capsular poly saccharides of Neisseria-meningitidis," NIPH Annals, 6 (1): 91-101 (1983).
Ip, C.C.Y. and Miller, W.J., "Monosaccharide Compositional Analysis of *Haemophilus influenzae* Type b Conjugate Vaccine. Method for In-Process Analysis", in Chromatography in Biotechnology, Chap. 10, pp. 132-143 (1993).

* cited by examiner

*Primary Examiner* — Oluwatosin Ogunbiyi
(74) *Attorney, Agent, or Firm* — Helen Lee; Robert Gorman; Otis Littlefield

(57) ABSTRACT

The invention is based on methods that allow analysis of mixed meningococcal saccharides from multiple serogroups even though they share monosaccharide units. With a combination of saccharides from serogroups C, W135 and Y, the invention analyses sialic acid, glucose and galactose content. The glucose and galactose results are used to directly quantify saccharides from serogroups Y and W135, respectively, and the combined glucose and galactose content is subtracted from the sialic acid content to quantify saccharides from serogroup C. The three serogroups can thus be resolved even though their monosaccharide contents overlap. The three different monosaccharide analyses can be performed on the same material, without interference between the monosaccharides and without interference from any other saccharide materials in the composition (e.g. lyophilisation stabilisers). The method can be used to analyse total and free saccharide in conjugate vaccines and simplifies quality control of vaccines containing capsular saccharides from multiple serogroups.

17 Claims, 8 Drawing Sheets

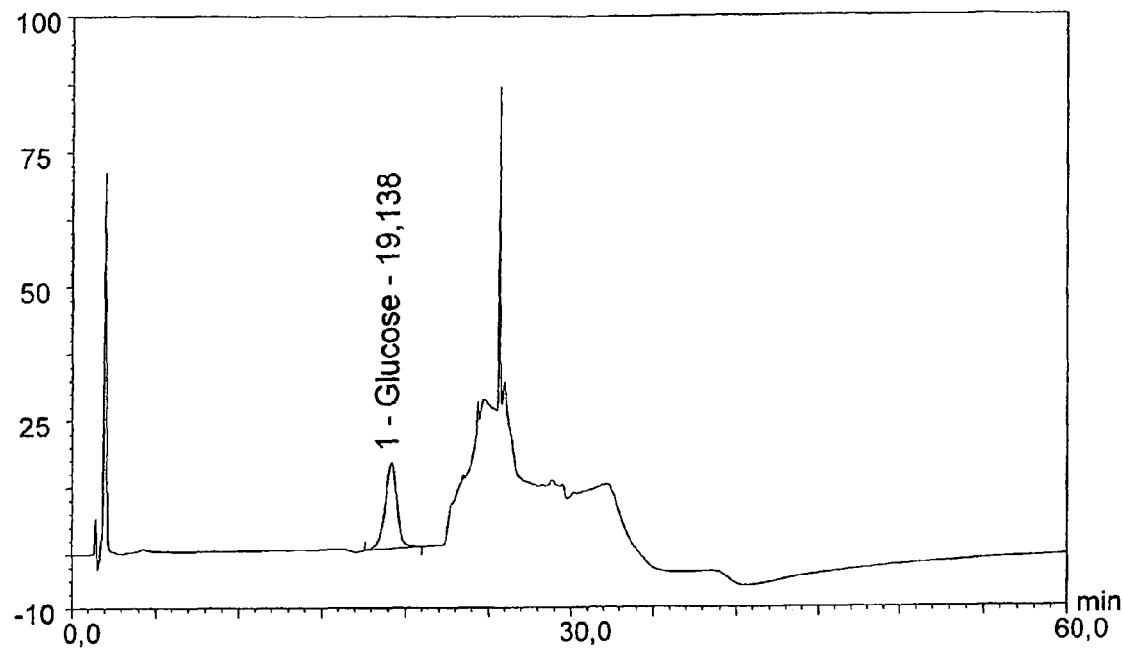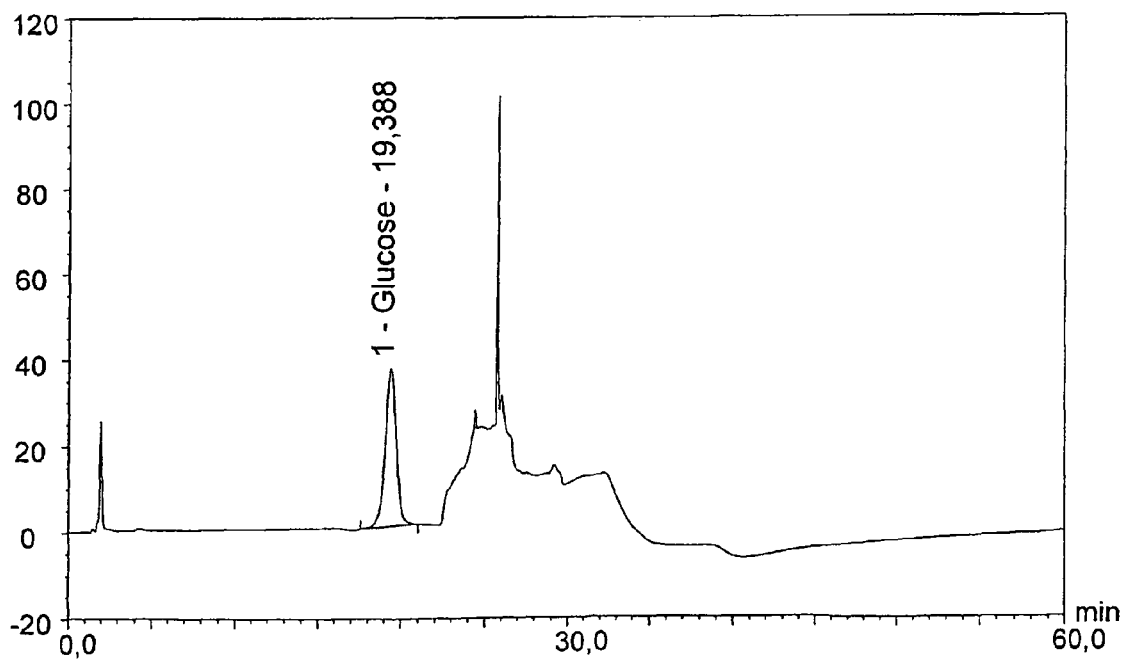

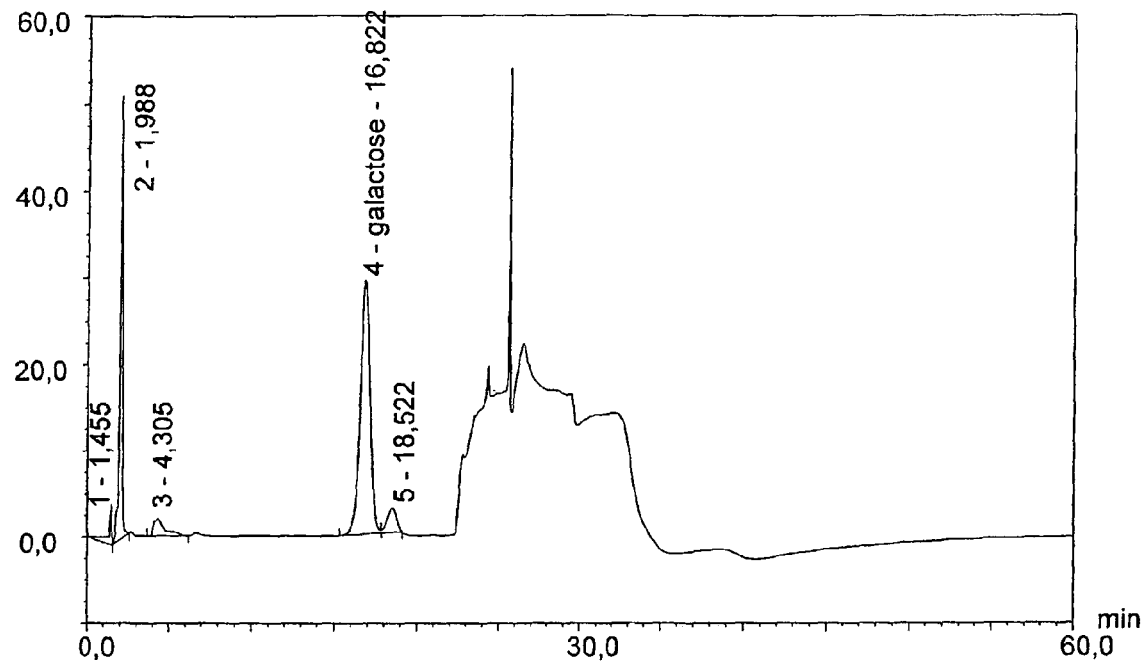
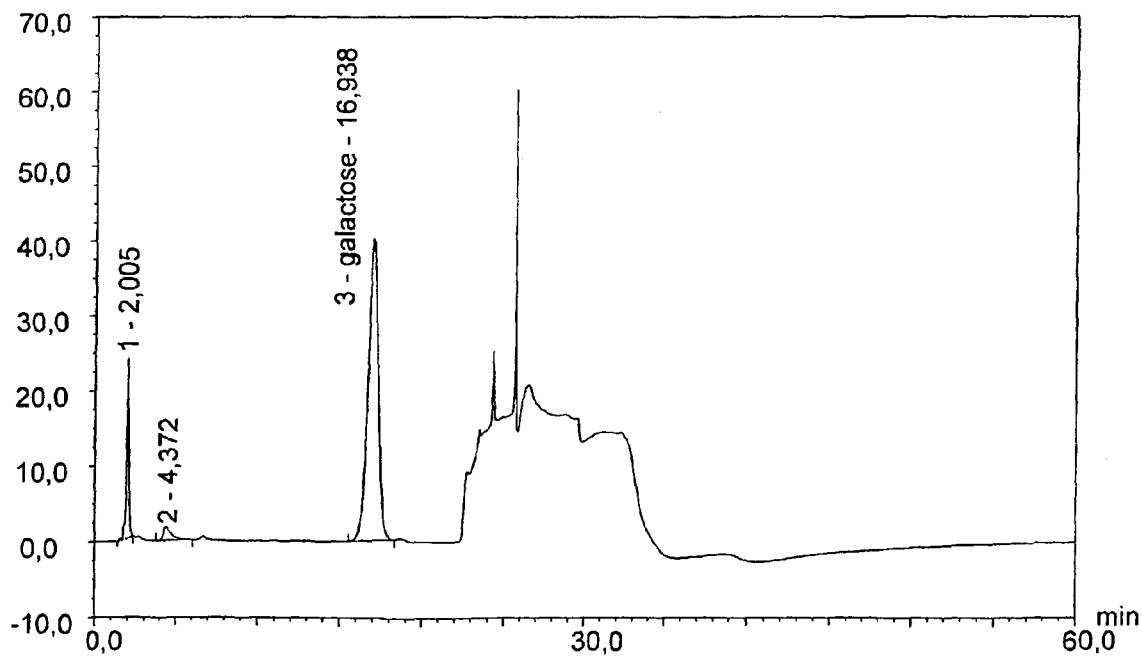

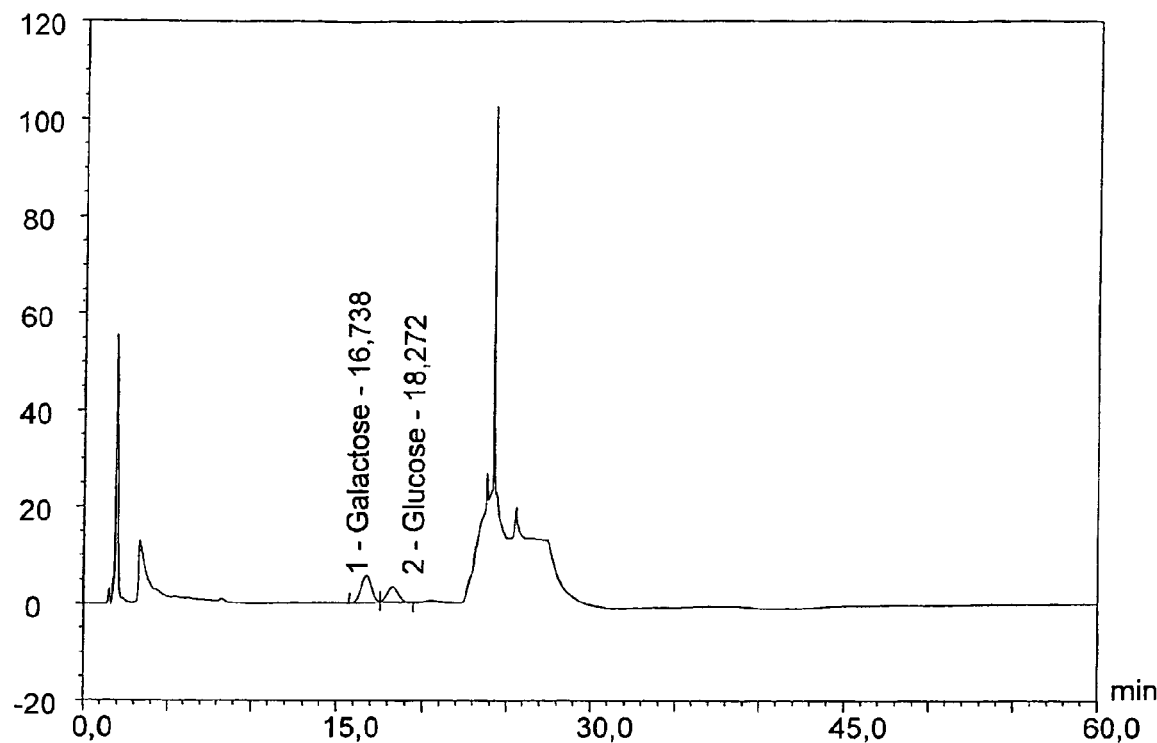
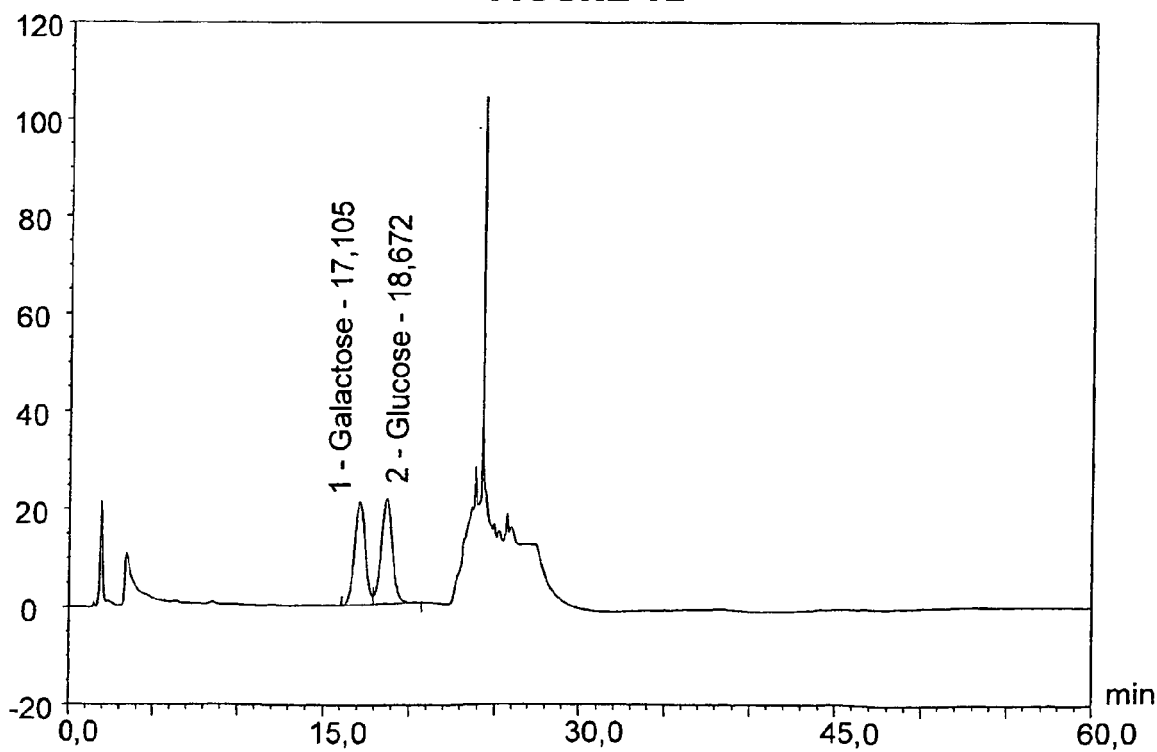

R = -H, -COCH3

ANALYSIS OF SACCHARIDE VACCINES WITHOUT INTERFERENCE

RELATED APPLICATIONS

This application is the U.S. National Phase of International Application No. PCT/IB2005/000987, filed Mar. 17, 2005 and published in English, which claims priority to Great Britain Application No. 0406013.3, filed Mar. 17, 2004. The teachings of the above applications are incorporated in their entirety by reference.

TECHNICAL FIELD

This invention is in the field of analysis and quality control of vaccines that include bacterial capsular saccharides, and in particular those where the saccharides are conjugated to a carrier.

BACKGROUND ART

Immunogens comprising capsular saccharide antigens conjugated to carrier proteins are well known in the art. Conjugation converts T-independent antigens into T-dependent antigens, thereby enhancing memory responses and allowing protective immunity to develop, and the prototype conjugate vaccine was for *Haemophilus influenzae* type b (Hib) [e.g. see chapter 14 of ref. 1]. Since the Hib vaccine, conjugated saccharide vaccines for protecting against *Neisseria meningitidis* (meningococcus) and against *Streptococcus pneumoniae* (pneumococcus) have been developed. Other organisms where conjugate vaccines are of interest are *Streptococcus agalactiae* (group B *streptococcus*) [2], *Pseudomonas aeruginosa* [3] and *Staphylococcus aureus* [4].

Conjugate vaccines for *N. meningitidis* serogroup C have been approved for human use, and include Menjugate™ [5], Meningitec™ and NeisVac-C™. Mixtures of conjugates from each of serogroups A, C, W135 and Y have been reported [e.g. refs. 6-9], including the Menactra™ product. Other mixtures of conjugated antigens include: (i) meningococcal A/C mixtures [10,11]; (ii) the PrevNar™ product [12] containing seven pneumococcal conjugates; (iii) mixed meningococcal and Hib conjugates [13,14]; and (iv) combined meningococcal, pneumococcal and Hib conjugates [15].

Issues when dealing with conjugate vaccines include stability and batch-to-batch consistency. In Hib vaccines, for instance, catalytic depolymerisation of the saccharide has been reported [16], and conjugates of the serogroup A meningococcus capsule are readily hydrolysed [17]. Instability of conjugates undesirably leads to a reduction in effective dose of immunogenic conjugate over time, variation between batches, and increases levels of uncharacterised breakdown products. References 18 & 19 discuss issues concerning stability testing of Hib conjugate vaccines.

Quantitative glycoconjugate analysis typically involves a first step of saccharide hydrolysis, with analysis then being based on the released monosaccharides. Whereas this analysis is relatively straightforward for single conjugates (e.g. anion-exchange chromatographic methods have been used for analysing hydrolysed conjugates of Hib [20] and serogroup A meningococcus [21]), the situation is more complex in combination vaccines, particularly where different saccharides share monosaccharide units. For example, the capsular saccharides of meningococcal serogroups C, W135 and Y all contain sialic acid, so any method based on measurement of released sialic acid will not be able to distinguish the three serogroups.

It is an object of the invention to provide improvements in quantitative assessment of saccharides in conjugate vaccines for assessing stability and integrity. In particular, it is an object to provide methods that can be used to measure individual conjugates within combined meningococcal conjugate vaccines, and thus to provide improvements in vaccine quality control and consistency.

DISCLOSURE OF THE INVENTION

The invention is based on methods that allow analysis of mixed meningococcal saccharides from multiple serogroups even though the saccharides share monosaccharide units. The invention thus provides a process for analysing the saccharide content of a composition, wherein:

(a) the composition comprises a capsular saccharide from serogroup C of *Neisseria meningitidis* and one or both of: (i) a capsular saccharide from serogroup W135 of *Neisseria meningitidis*; and/or (ii) a capsular saccharide from serogroup Y of *Neisseria meningitidis*;

(b) the process comprises a step of analysing the sialic acid content of the composition, and: (i) if the composition includes a serogroup W135 saccharide, a step of analysing the galactose content of the composition; (ii) if the composition includes a serogroup Y saccharide, a step of analysing the glucose content of the composition;

(c) if the composition includes a serogroup W135 saccharide, the content of serogroup W135 saccharide in the composition is determined according to the results of the galactose analysis from step (b);

(d) if the composition includes a serogroup Y saccharide, the content of serogroup Y saccharide in the composition is determined according to the results of the glucose analysis from step (b);

(e) the content of serogroup C saccharide in the composition is determined by comparing the results of the sialic acid analysis with: (i) if the composition includes a serogroup W135 saccharide but not a serogroup Y saccharide, the results of the galactose analysis from step (b); (ii) if the composition includes a serogroup Y saccharide but not a serogroup W135 saccharide, the results of the glucose analysis from step (b); or (iii) if the composition includes both a serogroup W135 saccharide and a serogroup Y saccharide, the combined results of the glucose and galactose analyses from step (b).

With a combination of saccharides from serogroups C, W135 and Y, therefore, the invention analyses sialic acid, glucose and galactose content. The glucose and galactose results are used to directly quantify saccharides from serogroups Y and W135, respectively, and the combined glucose and galactose content is subtracted from the sialic acid content to quantify saccharides from serogroup C. The three serogroups can thus be resolved even though their monosaccharide contents overlap. The inventors have advantageously found that the three different monosaccharide analyses can be performed on the same material, without interference between the monosaccharides and without interference from any other saccharide materials in the composition (e.g. lyophilisation stabilisers). The method can be used to analyse total and free saccharide in conjugate vaccines and simplifies quality control of vaccines containing capsular saccharides from multiple serogroups.

A method for analysing mixtures of aldose, hexosamine and sialic acid without interference has been described [22], but it relies on enzymatic treatments and chemical derivatisation. In contrast, the process of the invention does not require such steps and is thus quicker and easier to perform.

Moreover, the situation addressed in reference 22 does not suffer from the inherent problem of having to resolve different saccharides that share common monosaccharide units.

The invention also provides a computer apparatus adapted to perform a process of the invention. In particular, the invention provides a computer program for analysing the saccharide content of a composition as defined above, comprising a program module for: (a) receiving data on the sialic acid content, and on the glucose and/or galactose content, of a sample; and (b) calculating from those data the content of capsular saccharide from serogroup C and from serogroup W135 and/or Y. The invention also provides a computer program product comprising a computer readable storage medium having stored thereon the computer program of the invention.

The Capsular Saccharides of Serogroups C, W135 and Y

The methods of the invention are for analysing mixtures of meningococcal capsular saccharides. The mixtures include the capsular saccharides from (i) serogroup C and (ii) either or both of serogroups W135 and Y, i.e. C+W135, C+Y, or C+W135+Y. Further saccharides may also be present.

The serogroup C capsular saccharide is a homopolymer of ($\alpha 2 \rightarrow 9$)-linked sialic acid (N-acetyl neuraminic acid, or 'NeuNAc'). Most serogroup C strains have O-acetyl groups at C-7 and/or C-8 of the sialic acid residues, but about 15% of clinical isolates lack these O-acetyl groups [23,24]. The acetylation does not seem to affect protective efficacy (e.g. unlike the Menjugate™ product, the NeisVac-C™ product uses a de-O-acetylated saccharide, but both vaccines are effective). The saccharide structure is shown in FIG. 13 and is written as: →9)-NeupNAc 7/8 OAc-($\alpha 2 \rightarrow$ The serogroup W135 saccharide is a polymer of sialic acid-galactose disaccharide units. Like the serogroup C saccharide, it has variable O-acetylation, but at sialic acid 7 and 9 positions [25]. The structure is shown in FIG. 14 and is written as: →4)-D-Neup5Ac(7/9OAc)-$\alpha$-(2→6)-D-Gal-$\alpha$-(1→

The serogroup Y saccharide is similar to the serogroup W135 saccharide, except that the disaccharide repeating unit includes glucose instead of galactose (see FIG. 16). Like the serogroup W135 saccharide, it has variable O-acetylation at sialic acid 7 and 9 positions [25]. The serogroup Y structure is shown in FIG. 15 and is written as: →4)-D-Neup5Ac(7/9OAc)-$\alpha$-(2→6)-D-Glc-$\alpha$-(1→

Within a composition including capsular saccharides from serogroups C, W135 and Y there are thus three different constituent monomers (glucose, galactose and sialic acid), and these three monomers are present in a post-hydrolysis mixture. The quantity of glucose monomers in such a mixture is directly related to the quantity of serogroup Y saccharide in the original composition, and the quantity of galactose monomers is directly related to the quantity of W135 saccharide. For serogroup C, however, the situation is more complex: sialic acid is the only monomer available for quantifying the serogroup C saccharide, but any measurement of the quantity of sialic acid in the mixture will include monomers derived from the serogroup W135 and Y saccharides. The invention overcomes the complexity of this analysis by measuring the content in the mixture of each of galactose, glucose and sialic acid (separately and/or simultaneously), and then: (a) using the galactose content to quantify the pre-hydrolysis serogroup W135 content; (b) using the glucose content to quantify the pre-hydrolysis serogroup Y content; (b) using the difference between the sialic acid content and the combined glucose & galactose content to quantify the pre-hydrolysis serogroup C content i.e. the molar amount of serogroup C is calculated according to the molar amount of sialic acid minus the molar amount of (glucose+galactose). Subtraction of the molar glucose and galactose content from the molar sialic acid content corrects for interference from serogroups W135 and Y and leaves only sialic acid from serogroup C.

The invention can be used to analyse capsular saccharides of varying lengths. For example, Menjugate™ and Meningitec™ include size-selected fragments (oligosaccharides) of the full-length serogroup C polysaccharide, whereas NeisVac-C™ uses full-length polysaccharide. The invention can be used with oligosaccharides and/or with full-length polysaccharides. Oligosaccharides have a degree of polymerisation (DP) less than that found in native capsular polysaccharides present in bacteria, and may have an average DP <30 e.g. between 10 and 25. DP can conveniently be measured by ion exchange chromatography or by colorimetric assays [26].

Analysing Monosaccharide Content

The process of the invention involves a step analysing the content of sialic acid, of galactose (if serogroup W135 is present) and of glucose (if serogroup Y is present). If a process is being performed to monitor the presence of monosaccharide units in a composition (e.g. simply to monitor residual monosaccharides from an earlier stage in production, or to monitor possible hydrolytic release of monomers from a conjugate) then it can be performed on the composition directly. Typically, however, the process will be used for measuring total saccharide content of a composition, and so the composition will be hydrolysed to monosaccharides prior to the analysis. Thus the process of the invention will typically include a step of treating the composition in order to depolymerise the capsular saccharides to give their constituent monosaccharides. Analysis of sialic acid content and of galactose and/or glucose content can then proceed on the depolymerised mixture of released monosaccharides.

Conditions for depolymerisation of capsular saccharides to their constituent monosaccharides are known in the art. For example, the serogroup C saccharide can be hydrolysed for total saccharide content analysis by treatment with 100 mM HCl at 80° C. for 2 hours [27]. Acid hydrolysis using trifluoroacetic acid (TFA) can be used for hydrolysis of all of serogroups C, W135 and Y, with a slightly lower incubation temperature being preferred for serogroup C to avoid degradation of its sialic acid (90° C. rather than 100° C.). A typical TFA treatment involves addition of TFA to a final concentration of 2 M, followed by heating to 90-100° C. for 90 minutes. After depolymerisation, saccharide hydrolysates may be dried e.g. using a vacuum drier.

After depolymerisation, a composition will contain mixed monosaccharides derived from serogroups C and W135 &/or Y. The quantities of these monosaccharides in the mixture are directly related to the quantities of saccharides in the original pre-hydrolysis composition, and so quantities of the starting saccharides can be determined as described above. Quantities can be determined in terms of numbers (e.g. moles) of molecules, masses, ratios or concentrations. It is typical to work in moles, as sialic acid has a different molecular mass from glucose/galactose, but any of these measures can be used and interchanged to assess saccharide content of the mixtures. For quantitative measurement, analytical results may be compared to a standard with a known content of a particular saccharide.

The depolymerised mixture is preferably hydrolysed completely to monosaccharides. The inventors have found that incomplete hydrolysis sometimes occurs, giving mixtures in which disaccharide fragments are present (i.e. Gal-NeuNAc for MenW135, and Glc-NeuNAc for MenY). However, the monosaccharides are released with the correct theoretical ratio, and the disaccharides do not interfere with analysis of the monosaccharide, so their presence need not cause difficulties.

Progress of depolymerisation (e.g. to check for total hydrolysis to monosaccharides rather than partial hydrolysis to oligosaccharides) can be checked by measuring the degree of polymerisation (DP) in a mixture, using known techniques e.g. NMR, mass spectrometry, etc.

Methods for quantifying glucose, galactose and sialic acid monosaccharides are well known in the art. Methods may be direct or indirect (e.g. they may involve derivatisation of the monosaccharides followed by an analysis that correlates with original monosaccharide content). Methods may involve separation of the two/three different monosaccharides from each other, followed by separate analysis, and in such a case the actual measurement of mono saccharide content could be the same in each case, with specificity arising from the separation. It is preferred, however, to use methods which can analyse the saccharides in each other's presence, such that they do not need to be separated from each other before analysis. In addition, methods may be used for conjugated saccharides in which, after deconjugation, the carrier and the saccharide need not be separated. One preferred method is anion chromatography, and in particular high performance anion exchange chromatography (HPAEC), usually with pulsed amperometric detection (PAD) [28,29]. HPAEC-PAD systems are provided by Dionex™ Corporation (Sunnyvale, Calif.) e.g. the BioLC™ system, using a column such as PA1 [10 μm diameter polystyrene substrate 2% crosslinked with divinylbenzene, agglomerated with 500 nm MicroBead quaternary ammonium functionalized latex (5% crosslinked)] or PA10 [10 μm diameter ethylvinylbenzene substrate 55% crosslinked with divinylbenzene, agglomerated with 460 nm MicroBead difunctional quaternary ammonium ion (5% crosslinked)]. These systems can quantitatively analyse individual saccharides within mixtures without the need for derivatisation or pre-analysis separation. For saccharide analysis, it may be desired to filter other compounds before entry to the column, and Dionex™ produces pre-column traps and guards for this purpose e.g. an amino trap for removing amino acids, a borate trap, etc.

An alternative method for quantifying glucose, galactose and sialic acid monosaccharides within a depolymerised mixture is nuclear magnetic resonance (NMR). For ease of use and for high sensitivity, however, the chromatographic methods of the invention are preferred.

Once sialic acid content and glucose and/or galactose content have been determined, it is simple to compare the mole amounts of each monosaccharide in the mixture, and thereby calculate the quantity of capsular saccharides in the original composition.

The process of the invention is typically destructive. Rather than perform the process on a complete composition, therefore, it is more typical to take a sample from a composition of interest and then perform the analysis on the sample.

Conjugates

The invention is useful for analysing saccharide content of vaccines, and in particular for vaccines that include a conjugated saccharide. Covalent conjugation is used to enhance immunogenicity of saccharides by converting them from T-independent antigens to T-dependent antigens, thus allowing priming for immunological memory. Conjugation is particularly useful for paediatric vaccines and is a well known technique [e.g. reviewed in refs. 30 to 39]. Saccharides may be linked to carriers directly [40, 41], but a linker or spacer is generally used e.g. adipic acid, β-propionamido [42], nitrophenyl-ethylamine [43], haloacyl halides [44], glycosidic linkages [45], 6-aminocaproic acid [46], ADH [47], $C_4$ to $C_{12}$ moieties [48], etc.

Typical carrier proteins in conjugates are bacterial toxins or toxoids, such as diphtheria toxoid or tetanus toxoid. The $CRM_{197}$ diphtheria toxin derivative [49-51] is the carrier protein in Menjugate™ and Meningitec™, whereas tetanus toxoid is used in NeisVac™. Diphtheria toxoid is used as the carrier in Menactra™. Other known carrier proteins include the *N. meningitidis* outer membrane protein [52], synthetic peptides [53,54], heat shock proteins [55,56], pertussis proteins [57,58], cytokines [59], lymphokines [59], hormones [59], growth factors [59], artificial proteins comprising multiple human $CD4^+$ T cell epitopes from various pathogen-derived antigens [60], protein D from *H. influenzae* [61,62], pneumococcal surface protein PspA [63], iron-uptake proteins [64], toxin A or B from *C. difficile* [65], etc. Compositions may use more than one carrier protein e.g. to reduce the risk of carrier suppression, and a single carrier protein might carry more than one saccharide antigen [66]. Conjugates generally have a saccharide:protein ratio (w/w) of between 1:5 (i.e. excess protein) and 5:1 (i.e. excess saccharide). Compositions may include free carrier protein in addition to the conjugates [67].

In general, compositions including conjugated saccharides can be analysed using the invention in two ways. First, the total saccharide concentration for each serogroup in a composition can be measured e.g. prior to release of a vaccine (for regulatory or quality control purposes), or to check concentrations after conjugates are mixed. Second, free unconjugated saccharide in a composition can be measured e.g. to check for incomplete conjugation, or to follow conjugate hydrolysis by monitoring increasing free saccharide over time. By performing both types of analysis, the ratio of free saccharide to total saccharide can be assessed for each serogroup, which can be used for regulatory or quality control purposes. In general, it is desirable to ensure that a vaccine includes <25% (e.g. <20%, <15%, <10% etc.) of each saccharide in free form. High levels of free saccharides mean a lower immunogenic dose of conjugate.

Thus the invention provides a method for analysing a composition, wherein:
(a) the composition comprises a conjugate of a capsular saccharide from serogroup C of *Neisseria meningitidis* and one or both of: (i) a conjugate of a capsular saccharide from serogroup W135 of *Neisseria meningitidis*; and/or (ii) a conjugate of a capsular saccharide from serogroup Y of *Neisseria meningitidis*;
(b) the composition may comprise the capsular saccharides in unconjugated form;
(c) the content of any unconjugated capsular saccharides is determined by a process of the invention, as described above;
(d) the content of conjugated capsular saccharides is determined by a process of the invention, as described above; and, optionally:
(e) the ratio of conjugated:unconjugated saccharide is calculated for one or more of the capsular saccharides.

Steps (c) and (d) can be performed in either order, or simultaneously.

The invention also provides a method for releasing a vaccine for use by physicians, comprising the steps of: (a) manufacturing a vaccine containing a conjugate of a capsular saccharide from serogroup C of *Neisseria meningitidis* and one or both of: (i) a conjugate of a capsular saccharide from serogroup W135 of *Neisseria meningitidis*; and/or (ii) a conjugate of a capsular saccharide from serogroup Y of *Neisseria*

*meningitidis*; (b) analysing the amount of conjugated and/or unconjugated saccharide in the vaccine for each of said capsular saccharides; and, if the results from step (b) indicate a saccharide content acceptable for clinical use, (c) releasing the vaccine for use by physicians. Step (b) may involve assessment of minimum saccharide concentration (e.g. between 1-20 μg of total saccharide per serogroup), assessment of unconjugated:conjugated saccharide ratio (e.g. ≦20% by weight of unconjugated saccharide, preferably ≦10% or ≦5%), etc. Step (b) may be performed on a packaged vaccine, or may be performed on a bulk vaccine prior to packaging.

To separately assess conjugated and unconjugated saccharides, they must be separated. Free (i.e. unconjugated) saccharide in an aqueous composition can be separated from conjugated saccharide in various ways. The conjugation reaction changes carious chemical and physical parameters for the saccharide, and the differences can be exploited for separation. For example, size separation can be used to separate free and conjugated saccharide, as the conjugated material has a higher mass due to the carrier protein. Ultrafiltration is a preferred size separation method, and free saccharide can pass through an ultrafiltration membrane with an appropriate cut-off (e.g. 30 kDa for a $CRM_{197}$ carrier), whereas the conjugate will be retained. An alternative method is to use solid phase extraction using (SPE) a column or membrane that retains conjugate but that lets free saccharide pass through as an eluate. SPE tends to be more rapid and more consistent, but size separation is more universally-applicable. As a further alternative, if conjugates have been adsorbed to an adjuvant then centrifugation will separate adsorbed conjugate (pellet) from free saccharide (supernatant) that desorbs after hydrolysis.

Thus free saccharide can be separated from total saccharide and can be separately analysed, thereby allowing a determination of the amount of unconjugated material in a composition. Comparing the free amount to the total amount is easier than separately analysing the two pools after separation, particularly if the conjugated material is retained on a support during separation.

Further Capsular Saccharide Components

The invention allows analysis of compositions that comprise capsular saccharides from serogroups C and W135 &/or Y of *N. meningitidis*. It can also be used for analysis of compositions that include further capsular saccharides e.g. a capsular saccharide from serogroup A of *N. meningitidis*, a capsular saccharide from *H. influenzae* b, etc.

The capsular saccharide of serogroup A meningococcus is a homopolymer of (α1→6)-linked N-acetyl-D-mannosamine-1-phosphate, with partial O-acetylation in the C3 and C4 positions (FIG. 17). The acetyl groups can be replaced with blocking groups to prevent hydrolysis [17], and such modified saccharides are still serogroup A saccharides within the meaning of the present invention. Depolymerisation conditions for the serogroup A capsular saccharide are known [2]) e.g. hydrolysis by TFA at 100° C., as described above for other serogroups. An alternative method involves Dowex 50 H+ followed by heating for 1 hour at 100° C. [68]. Released mannosamine phosphate monomers can be analysed in parallel with glucose, galactose and sialic acid e.g. by HPAEC-PAD [21]).

The Hib capsular saccharide is a polymer of ribose, ribitol, and phosphate. The saccharide is known as 'PRP' (poly-3-β-D-ribose-(1,1)-D-ribitol-5-phosphate) and is shown in FIG. 18. Methods for depolymerising PRP to monosaccharides for HPAEC-PAD or $^{31}$P-NMR analysis are known e.g. by overnight incubation with NaOH at room temperature [20]. Released ribose and ribitol can be analysed in parallel with glucose, galactose and sialic acid.

The serogroup C capsular polysaccharide is a homopolymer of α2→9-linked sialic acids (also known as colominic acid). It is preferred that a composition analysed by the invention will not include any other homopolymers of sialic acid e.g. the capsular saccharide of serogroup B meningococcus (α2→8-linked sialic acids), or the capsular saccharide of *E. coli* K12 (with α2→8 and α2→9 links). More generally, if the composition to be analysed includes a capsular saccharide that includes a glucose, galactose or sialic acid monomer, then it is preferred that this capsular saccharide should also include further monomer or monomers that is/are unique (within the mixture) to that saccharide, in order to facilitate mixed analysis. Even where monomers are shared between saccharides, the presence of a unique monomer allows different saccharides to be analysed in parallel using the same principles as described for resolving serogroups C, W135 and Y of meningococcus.

Non-Capsular Saccharide Components

Where the invention relies on monosaccharide analysis of a mixture derived from a composition under analysis, it is preferred that the composition does not include that monosaccharide in free form (other than any background monosaccharides derived from capsular saccharide hydrolysis). For example, including free sialic acid in a composition to be analysed could result in the serogroup C content being overestimated. The same principle applies if disaccharides etc. are included and are then hydrolysed e.g. the presence of sucrose (glucose+fructose), or of maltose or trehalose (both di-glucose) could give an overestimate of serogroup Y content, and the presence of lactose (glucose+galactose) could give an overestimate of W135 and Y (and an underestimate of serogroup C).

However, such saccharides are often used in vaccine formulation (e.g. as stabilisers [69,70]), and there are two general ways in which these interference problems can be minimised or avoided. First, initial levels of these components can be measured, and then subtracted from the levels measured in the depolymerised mixture. Second, these components can be removed from the composition prior to analysis e.g. by filtration or dialysis. Ultrafiltration membranes can be used to remove low molecular weight components e.g. a 1K membrane to remove sucrose (MW: 360).

The presence of monosaccharides that are not also found in the capsular saccharides being analysed does not normally lead to interference problems. For example, sugar alcohols might be included in a vaccine as a lyophilisation stabiliser [71], but HPAEC-AED is able to distinguish between a simple monosaccharide and the corresponding polyol monosaccharide e.g. between the mannose (as found in the Aerobacter aerogenes capsule [72]) and mannitol (a stabiliser) monosaccharides, and between ribose and ribitol [73].

Analysis of Non-Saccharide Components

As well as analysing the content of saccharides in a composition, the process may include analysis of other components or properties e.g. osmolality, pH, degree of polymerisation for individual saccharides or conjugates, protein content (particularly for carrier proteins), aluminium content, detergent content, preservative content, etc.

The invention provides a method for preparing a vaccine composition, comprising a step of analysis of a composition according to the invention, including a step of pH measurement, followed by a step of adjusting the pH of the composition to a desired value e.g. between 6 and 8, or about 7.

The invention provides a method for packaging a vaccine, comprising the steps of: (a) manufacturing a bulk vaccine containing a conjugate of a capsular saccharide from serogroup C of *Neisseria meningitidis* and one or both of: (i) a conjugate of a capsular saccharide from serogroup W135 of *Neisseria meningitidis*; and/or (ii) a conjugate of a capsular saccharide from serogroup Y of *Neisseria meningitidis*; (b) analysing the amount of conjugated and/or unconjugated saccharide in the bulk vaccine for each of said capsular saccharides; (c) optionally, analysing the bulk vaccine for pH and/or other properties; and, if the results from step (b) and (c) indicate that the bulk vaccine is acceptable for clinical use, (d) preparing and packaging the vaccine for human use from the bulk. Step (c) may involve (see above) assessment of minimum saccharide concentration, assessment of unconjugated:conjugated saccharide ratio, etc. Step (d) may involve packaging into unit dose form or in multiple dose form e.g. into vials or into syringes. A typical human dose for injection has a volume of 0.5 ml.

Step (c) and/or (d) may be preceded by mixing the bulk vaccine with one or more further antigens e.g. with

- a capsular saccharide antigen from serogroup A of *N. meningitidis*.
- a protein antigen from serogroup B of *N. meningitidis*
- preparations of *N. meningitidis* serogroup B microvesicles [74], 'native OMVs' [75], blebs or outer membrane vesicles [e.g. refs. 76 to 81 etc.].
- a saccharide antigen from *Haemophilus influenzae* type b
- an antigen from *Streptococcus pneumoniae*, such as polyvalent conjugated saccharide antigens [e.g. refs. 82 to 84].
- an antigen from hepatitis A virus, such as inactivated virus [e.g. 85, 86].
- an antigen from hepatitis B virus, such as the surface and/or core antigens [e.g. 86, 87].
- an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 88 & 89]. Cellular pertussis antigens may be used.
- a diphtheria antigen, such as a diphtheria toxoid [e.g. chapter 13 of ref. 1] e.g. the $CRM_{197}$ mutant [e.g. 90].
- a tetanus antigen, such as a tetanus toxoid [e.g. chapter 27 of ref. 1].
- polio antigen(s) [e.g. 91, 92], such as IPV.

Such antigens may be adsorbed to an aluminium salt adjuvant (e.g. a hydroxide or a phosphate). Any further saccharide antigens are preferably included as conjugates.

Batch-to-Batch Consistency

For human vaccine manufacture, conjugated saccharides should be subject to quality control before conjugation (e.g. the saccharide and the carrier protein), after conjugation, after formulation and after mixing. Prior art methods based on monosaccharide analysis cannot be used to distinguish capsular saccharides from meningococcal serogroups C, W135 and Y after they have been mixed, because of the interference caused by having multiple sources of sialic acid. With the invention, however, monosaccharide analysis can be used to analyse mixed conjugates. Moreover, the processes of the invention are reliable and consistent, and thus allow valid comparisons of different batches of mixed conjugates, where this was not possible with prior art methods. Different batches of mixed conjugate vaccines can thus be prepared, assayed, and then the most consistent batches can be selected for release and use, whereas aberrant batches can be rejected.

The invention provides a process for quantifying saccharides from individual serogroups within a mixture of capsular saccharides from at least two different meningococcal serogroups, wherein: (a) the different serogroups comprise serogroup C and one or both of: (i) serogroup W135 and/or (ii) serogroup Y; (b) the process comprises a step of depolymerising the capsular saccharides within the mixture, to give a depolymerised mixture; and (c) the different serogroups are quantified by comparing the monosaccharide composition of the depolymerised mixture.

The invention also provides n batches of a vaccine, wherein: (a) each of the n batches of vaccine comprises: a conjugate of a capsular saccharide from serogroup C of *Neisseria meningitidis* and one or both of: (i) a conjugate of a capsular saccharide from serogroup W135 of *Neisseria meningitidis*; and/or (ii) a conjugate of a capsular saccharide from serogroup Y of *Neisseria meningitidis*; (b) the concentration of conjugated serogroup C saccharide in the first batch is $C_1$; (c) the concentration of conjugated serogroup C saccharide in the second batch is $C_2$; if applicable, (d) the concentration of conjugated serogroup W135 saccharide in the first batch is $W_1$; if applicable, (e) the concentration of conjugated serogroup W135 saccharide in the second batch is $W_2$; if applicable, (f) the concentration of conjugated serogroup Y saccharide in the first batch is $Y_1$; if applicable, (g) the concentration of conjugated serogroup Y saccharide in the second batch is $Y_2$; (h) the ratios $C_1/C_2$, $W_1/W_2$ and $Y_1/Y_2$ are each between 0.90 and 1.10, and preferably are each between 0.95 and 1.05; and (i) the value of n is 2 or more (e.g. 2, 3, 4, 5, 6, 7, 8, 9, 10, 11, 12, 13, 14, 15 or more).

The ratios specified in (h) may be based on a single sample from each batch being compared, but will typically be based on average values (e.g. means) from multiple samples of each batch. Thus each of the n batches may be subjected to multiple sampling, and each sample may be subjected to multiple measurements of $C_1$, $C_2$, $W_1$, $W_2$, $Y_1$, and $Y_2$, with averages then being calculated for each batch, and with the averages being used to calculate the necessary ratios.

Each batch (or lot) of vaccine will have been prepared separately. For example, two different batches can be made by separate mixings of the same bulk single conjugates, or by mixing bulk single conjugates that were separately prepared. Different samples of the same bulk mixture are not different batches, as these samples are not subject to the batch-to-batch variations that result from differences that arise when preparing mixtures of different conjugates.

In addition to characteristics (a) to (i) as specified above, the n batches may additionally be characterised by: (j) the concentration of unconjugated serogroup C saccharide in the first batch is $C_3$; (k) the concentration of unconjugated serogroup C saccharide in the second batch is $C_4$; if applicable, (l) the concentration of unconjugated serogroup W135 saccharide in the first batch is $W_3$; if applicable, (m) the concentration of unconjugated serogroup W135 saccharide in the second batch is $W_4$; if applicable, (n) the concentration of unconjugated serogroup Y saccharide in the first batch is $Y_3$; if applicable, (o) the concentration of unconjugated serogroup Y saccharide in the second batch is $Y_4$; (p) the ratios $C_3/C_4$, $W_3/W_4$ and $Y_3/Y_4$ are each between 0.90 and 1.10, and preferably are each between 0.95 and 1.05. The batches may also be characterised by: (q) the ratios $C_3/C_1$, $C_4/C_2$, $W_3/W_1$, $W_4/W_2$, $Y_3/Y_1$, and $Y_4/Y_2$ are each less than 0.20 (e.g. <0.15, <0.10, <0.05, <0.02, 0).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

It will be appreciated that sugar rings can exist in open and closed form and that, whilst closed forms are shown in structural formulae herein, open forms are also encompassed by the invention.

BRIEF DESCRIPTION OF DRAWINGS

FIGS. 5 and 6 show similar analyses for a serogroup Y conjugate that had not been lyophilised, and FIGS. 7 and 8 show the same analysis for a serogroup W135 conjugate.

FIGS. 9 to 12 show HPAEC-PAD analyses of mixed conjugates from serogroups C, W135 and Y.

MODES FOR CARRYING OUT THE INVENTION

Conjugate Production and Chromatographic Methods

Capsular saccharide antigens were prepared from serogroups A, C, W135 and Y of *Neisseria meningitidis* and conjugated to $CRM_{197}$ as described in reference 7.

The four conjugates were combined to give an aqueous "MenACWY" composition.

In separate work, the serogroup A conjugate was lyophilised in the presence of either sucrose or mannitol, and a mixture of the serogroup C, W135 and Y conjugates was prepared ("MenCWY").

Analysis of saccharide content was performed on a Dionex™ HPAEC-PAD chromatography system according to the manufacturer's instructions. The instrument had a gradient pump module (GP40 or GP50), a pulsed amperometric detector (ED40 or ED50) and an autosampler (AS3500 or AS50). Saccharides are detected by measuring electrical current generated by their oxidation at the surface of a gold working electrode (with Ag/AgCl reference electrode). A triple-potential waveform was applied using the following settings: E1=0.05 V; t1=400 ms; E2=0.75 V; t2=200 ms; E3=−0.15 V; t3=400 ms). Integration occurred from 200 to 400 ms during E1 application. The chromatographic data were integrated and processed using PeakNet 6.4 data reduction software.

Serogroup A

Figure 1:
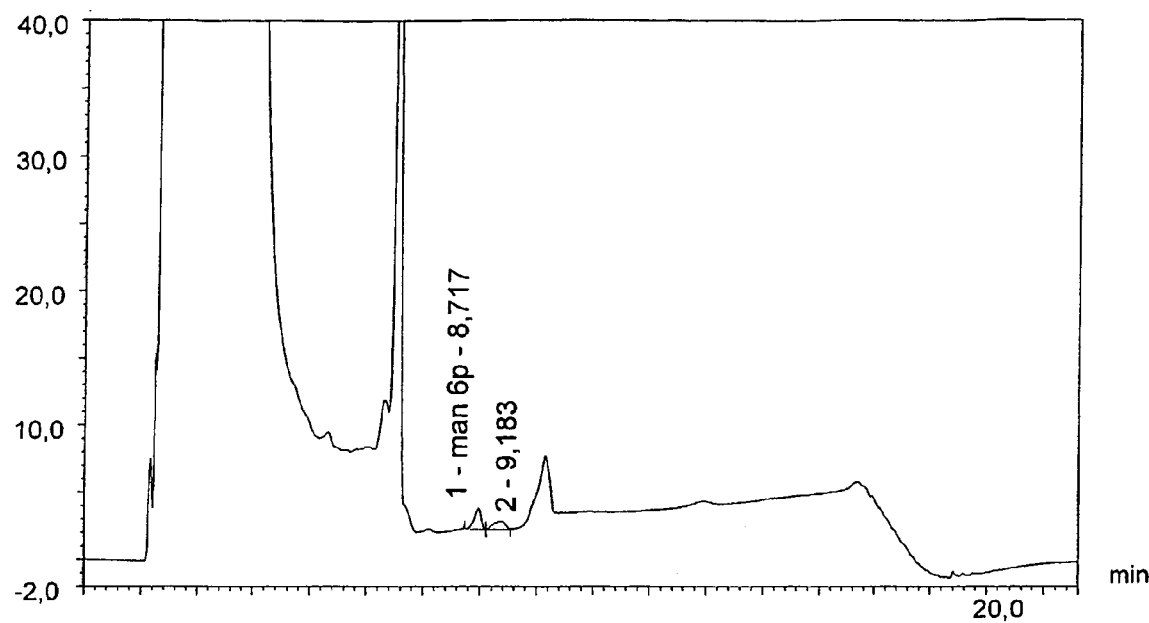
FIGS. 1 and 2 show HPAEC-PAD analysis of a meningococcal serogroup A conjugate, lyophilised using a mannitol stabiliser. Similar analyses for material where sucrose had been used as a stabiliser are shown in FIGS. 3 and 4.

The mannitol-lyophilised formulation of serogroup A saccharide was tested by HPAEC-PAD after storage at 4° C. for 3 months. Conjugate-containing compositions were separated from free saccharide using a C4 solid phase extraction (SPE) column. The solution containing free saccharide was subjected to acid hydrolysis using TFA at 100° C. for 2 hours. The mixture was then applied to a Dionex™ CarboPac PA1 column using a PA1 guard, gradient elution and PAD detection, for detection of mannosamine-6-phosphate. Results are shown in FIG. 1.

Figure 2:
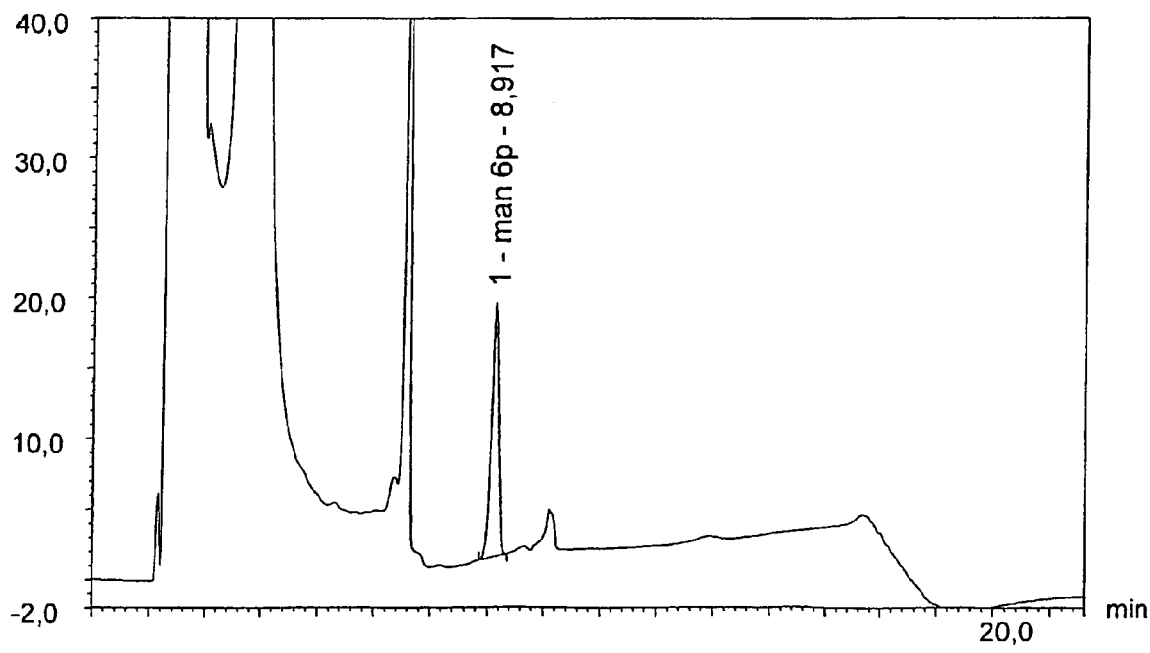

The same analysis was performed, but without SPE separation of free saccharide. The results of this analysis are shown in FIG. 2. Comparison of FIGS. 1 & 2, taking into account that the FIG. 1 analysis used a 1:2 dilution and the FIG. 2 analysis used a 1:5 dilution, shows that the mannosamine-6-phosphate peak is much lower in FIG. 1, showing a low level of free saccharide in the composition. Quantitative analysis shows 10.7 µg total saccharide per vial, with 3.7% free.

Figure 3:
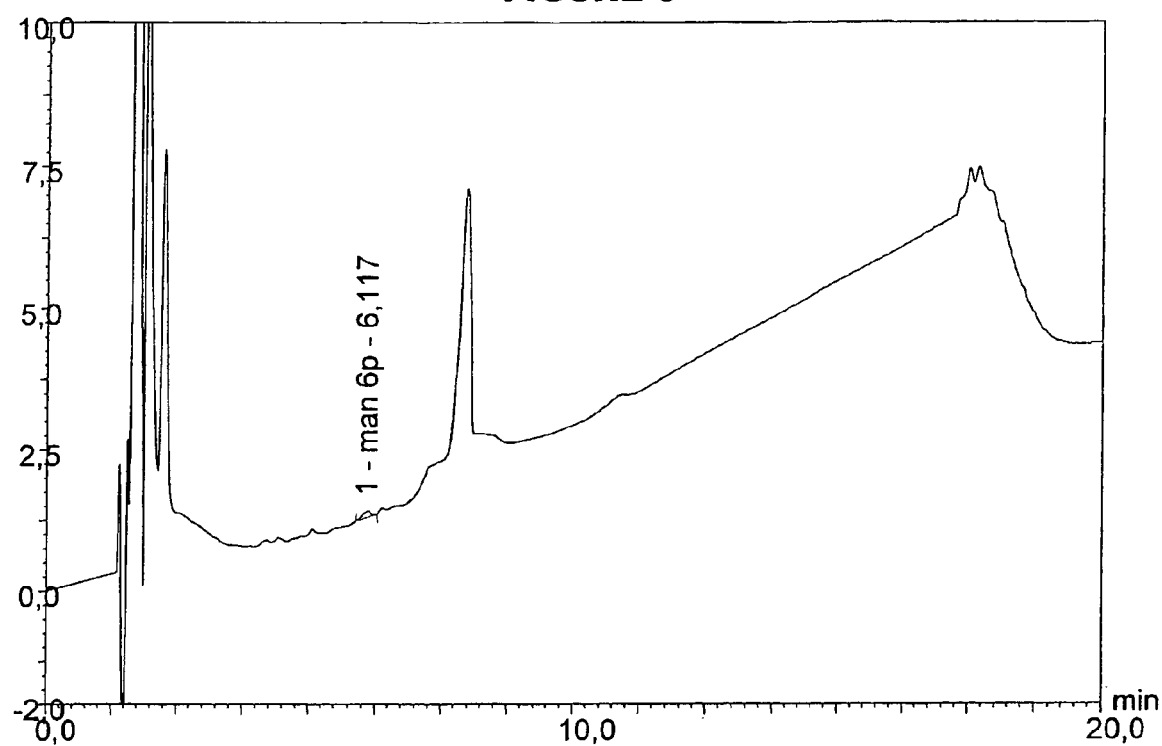
Figure 4:
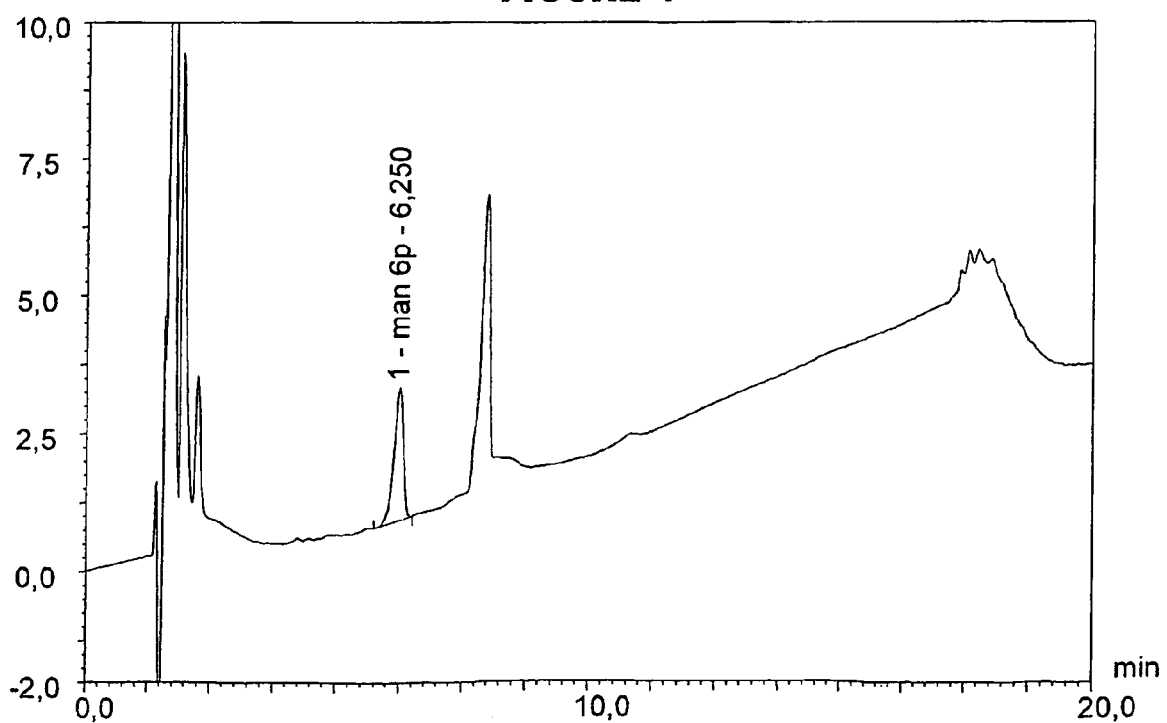

The sucrose-lyophilised material was analysed in the same way, after reconstitution with 600 µl water per vial, followed by pooling of samples to give 2-3 ml per analysis. Prior to the SPE C4, however, the composition was subjected to ultrafiltration using a 1K membrane (wash with 2 ml water, load 2 ml sample solution, 3 cycles of washing with 2 ml water each time, recover retentate and adjust volume up to 1 ml, dilute 1:1 to give final NaCl concentration of 0.9% for SPE loading). FIG. 3 shows that there was negligible free saccharide in the composition, but a large peak corresponding to conjugated material (FIG. 4).

Serogroups W135 and Y

Prior to combination with other conjugates, the bulk serogroup Y conjugate was analysed. The conjugate was separated from free saccharide using a 30 kDa ultrafiltration membrane. Material to be analysed was hydrolysed with TFA at 100° C., followed by quantitative analysis of glucose on the Dionex™ machine using a CarboPac PA1 column, an AminoTrap, an isocratic elution and regeneration step, and PAD detection, according to the manufacturer's instructions. $CRM_{197}$ carrier did not need to be removed before applying the hydrolysate to the column. Unconjugated material was detectable (FIG. 5) but was less abundant than the total glucose (FIG. 6). Taking the different dilutions into account, analysis of these Figures give a free saccharide fraction of 1.8%.

The bulk serogroup W135 material was treated and analysed in the same way, but with galactose detection rather than glucose detection (FIGS. 7 and 8). Taking the different dilutions into account, analysis of these Figures give a free saccharide fraction of 6%.

Combined Conjugates

The conjugates for serogroups A, C, W135 and Y were combined with an aluminium phosphate adjuvant, as described in reference 7. A MenCWY conjugate combination that had been stored for 2 weeks at 4° C. was used to reconstitute lyophilised MenA conjugate, and analysis followed 48 hours later, with centrifugation to separate the adjuvant from conjugates. The combined conjugates were separated from free saccharides by two cycles of ultrafiltration using a 30 kDa membrane. The second cycle decreased contamination with glycoconjugate which was sometimes found to pass through in the permeate of the first cycle. Saccharides were assayed, before and after ultrafiltration by acid hydrolysis using TFA at 90° C./100° C., followed by two separate HPAEC-PAD analyses using a Dionex™ CarboPac PA1 column.

Figure 9:
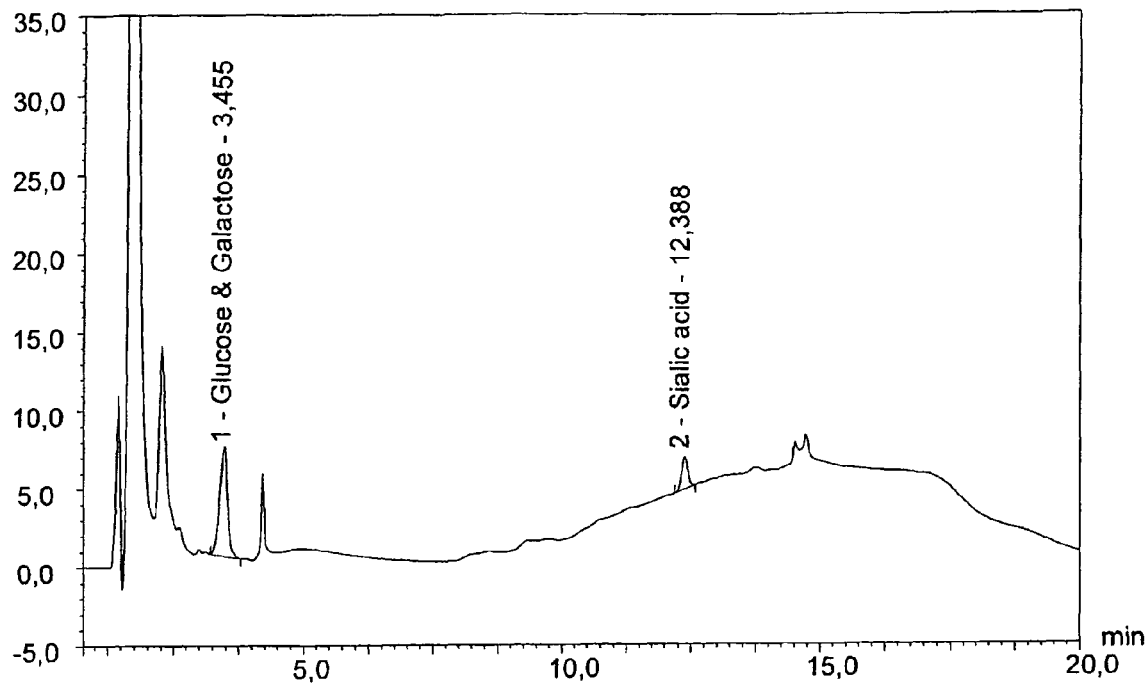
Figure 10:
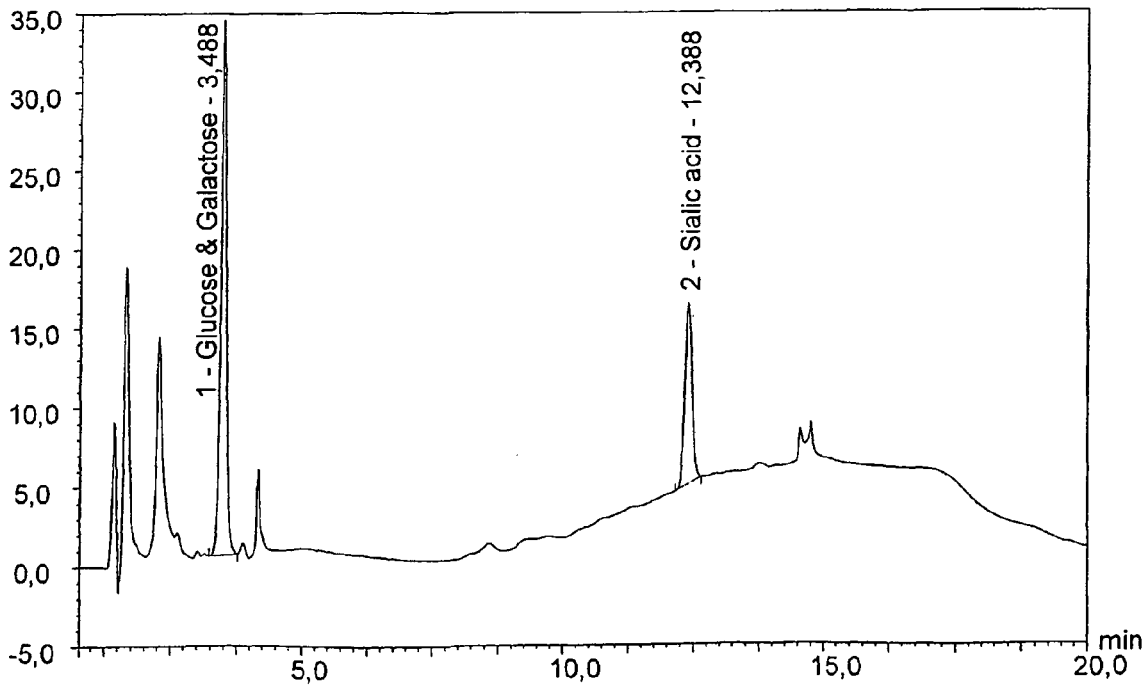
Figure 13:
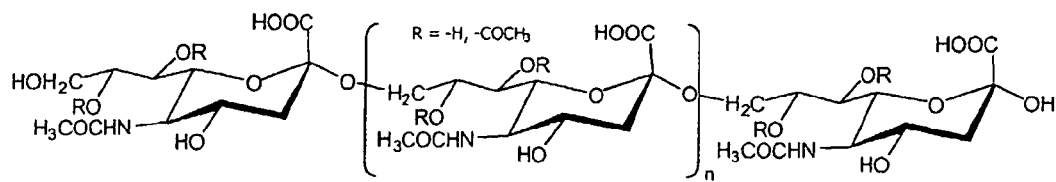
FIGS. 13 to 15 show structural formulae for the capsular saccharides of meningococcal serogroups C (13), W135 (14), and Y (15).
Figure 14:
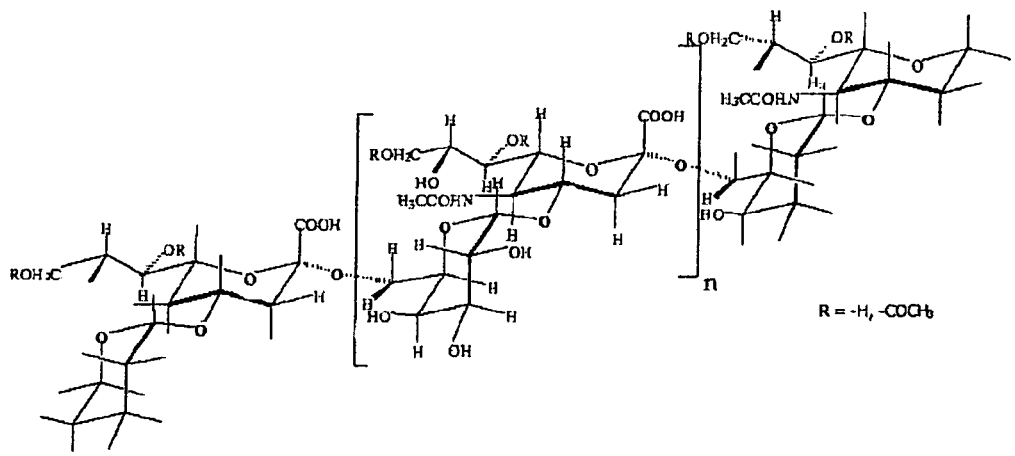
Figure 15:
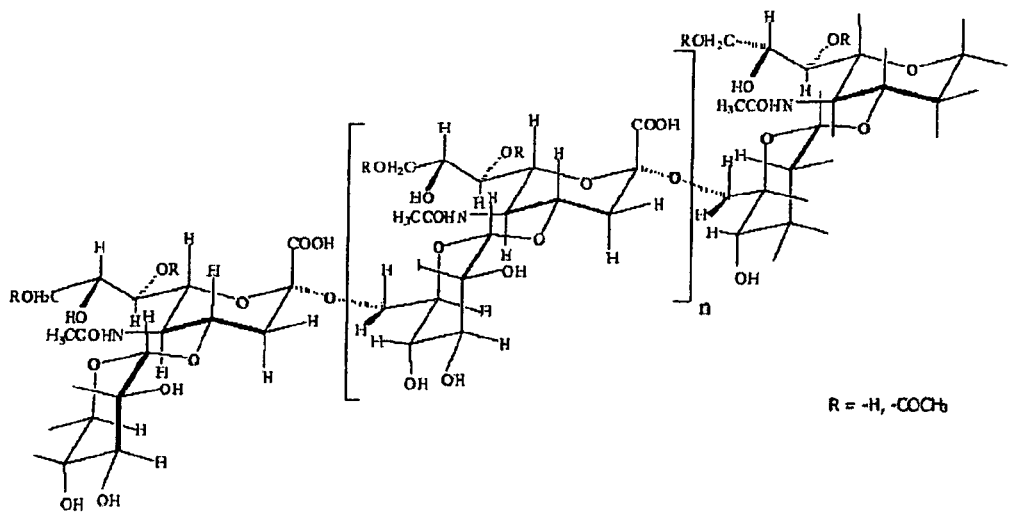
Figure 16:
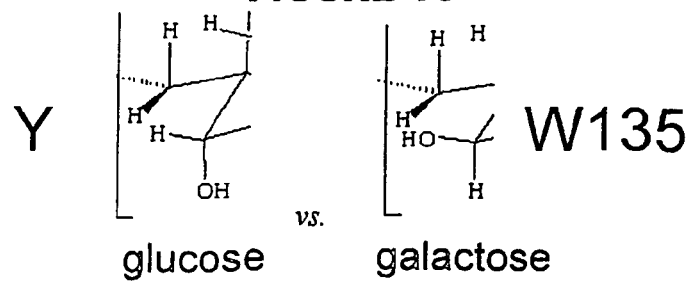
FIG. 16 shows the difference between serogroups W135 and Y.
Figure 17:
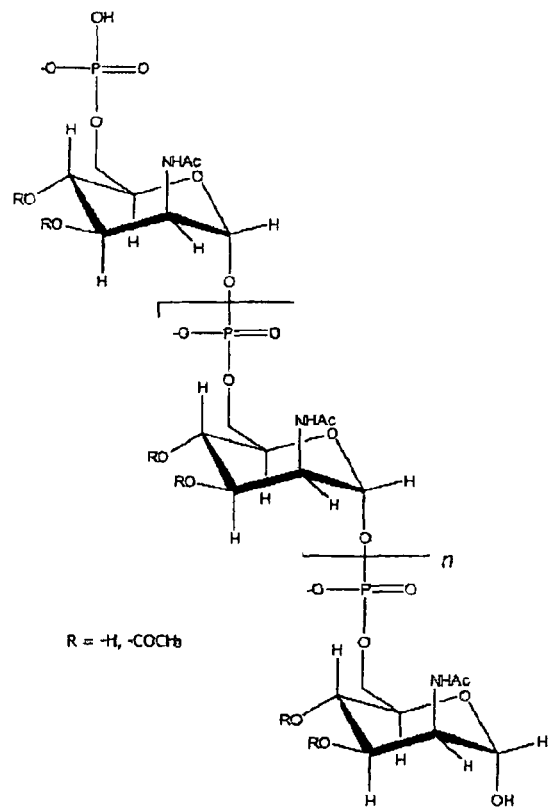
FIG. 17 shows a structural formula of the capsular saccharide from serogroup A meningococcus.
Figure 18:
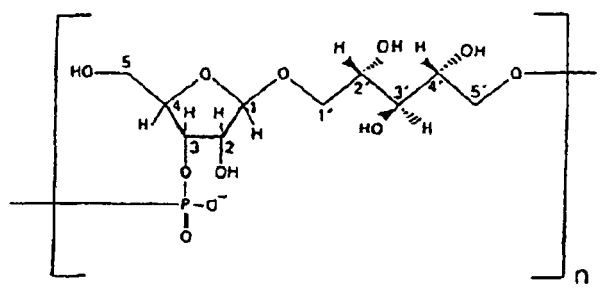
FIG. 18 shows a structural formula of the capsular saccharide from *H. influenzae* type b

For serogroup C analysis, the column had a CarboPac PA1 guard and used gradient step elution. This column was run in a mode where glucose and galactose are not resolved, as it is more rapid this way. Results are shown in FIGS. 9 and 10. For serogroups W135 and Y, the column had an AminoTrap and used isocratic elution and regeneration, which resolves glucose and galactose. Results are shown in FIGS. 11 and 12.

To calculate the quantities of each different saccharide, the quantity of sialic acid in the FIG. 9/10 analysis is corrected for interference by subtracting the combined quantity of glucose and galactose. This value gives the MenC concentration. The quantities of galactose and glucose in the FIG. 11/12 analysis are then used to quantify serogroups W135 and Y. The combined quantities of glucose and galactose from FIG. 11/12 may not match the quantity taken from FIG. 9/10 because of incomplete hydrolysis, as described above, but such discrepancies do not affect the overall analysis. Quantities were calculated by comparison to standards containing known amounts of glucose, galactose and sialic acid.

A typical duplicate analysis of total and free MenC saccharide in a conjugate gave these results:

| Sample | Glc + Gal (nmol/ml) | Total SA (nmol/ml) | Difference (nmol/ml) | Dilution | MenC (µg/ml)† | Mean | Free MenC |
|---|---|---|---|---|---|---|---|
| Total | 9.26 | 14.93 | 5.67 | 10× | 17.5 | 17.6 | <5% |
|  | 8.72 | 14.46 | 5.74 |  | 17.8 |  |  |
| Free | 2.45 | 2.35 | 0.10 | 2× | <1.0 | <1.0 |  |
|  | 2.53 | 2.33 | 0.20 |  | <1.0 |  |  |

† i.e. concentration of serogroup C saccharide.

Despite the lack of a unique saccharide for quantifying the serogroup C saccharide, therefore, the invention allows this material to be quantitatively assayed in a background of serogroup W135 and Y saccharides.

Similar analysis of FIGS. 9 and 11 reveals the amount of each free saccharide in the MenACWY composition, and allows free saccharide to be expressed as a percentage of the total saccharide in the composition. This analysis was performed at various time points over a 1 year period for a MenCWY combination formulated to contain 10 µg/dose (i.e. 20 µg/ml) of each saccharide. Results were:

|  |  | Time (weeks) | | | | | | | | |
|---|---|---|---|---|---|---|---|---|---|---|
|  |  | 0 | 2 | 4 | 13 | 34 | 52 | Mean | SD | CV |
| C | Total (µg/ml) | 18.3 | 20.3 | 22.6 | 23.6 | 21.3 | 20.5 | 21.1 | 1.86 | 8.8 |
|  | Free (%) | 5.0 | 5.0 | 5.0 | 5.0 | 5.2 | 5.0 | — | — | — |
| W | Total (µg/ml) | 21.0 | 20.3 | 20.1 | 21.7 | 20.2 | 21.9 | 20.9 | 0.79 | 3.8 |
|  | Free (%) | 10.7 | 11.2 | 10.1 | 8.8 | 9.8 | 9.9 | — | — | — |
| Y | Total (µg/ml) | 19.5 | 17.3 | 17.0 | 18.7 | 19.1 | 22.4 | 19.0 | 1.94 | 10.2 |
|  | Free (%) | 5.6 | 6.7 | 5.3 | 6.3 | 5.3 | 10.8 | — | — | — |

SD = standard deviation
CV = coefficient of variation i.e. (SD/mean) × 100%

Figure 19:
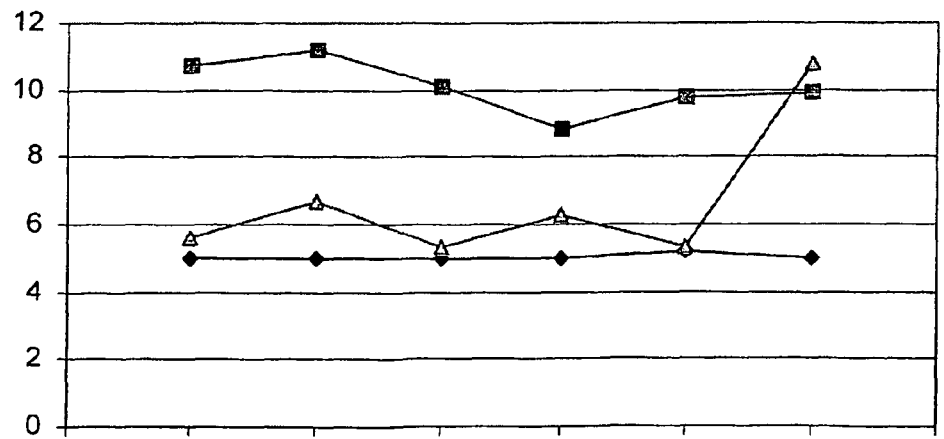
FIG. 19 shows the change in free saccharide (%) over six time points in combined conjugates from serogroups C (♦), W135 (■) and Y (▲).

The variation in % free saccharide at the six time points is shown in FIG. 19.

In a second series of experiments, vaccines were formulated at half (5 µpg of each saccharide per dose) and quarter dose (2.5 µg) relative to the previous work. The process of the invention was used to resolve the different saccharides from within the combination, and results were:

| 5 µg/dose (10 µg/ml) | | | | | | |
|---|---|---|---|---|---|---|
| | Time (months) | | | | | |
| | | 0 | 1 | 3 | Mean | SD | CV |
| C | Total (µg/ml) | 8.0 | 9.1 | 8.2 | 8.43 | 0.59 | 7.0% |
|  | Free (%) | <10.0 | <10.0 | <10.0 | — | — | — |
| W | Total (µg/ml) | 9.4 | 9.8 | 8.9 | 9.37 | 0.45 | 4.8% |
|  | Free (%) | <10.6 | 11.5 | <10.6 | — | — | — |
| Y | Total (µg/ml) | 10.5 | 12.3 | 11.2 | 11.33 | 0.91 | 8.0% |
|  | Free (%) | <10.6 | <10.6 | <10.6 | — | — | — |

| 2.5 µg/dose (5µg/ml) | | | | | | |
|---|---|---|---|---|---|---|
| | Time (months) | | | | | |
| | | 0 | 1 | 3 | Mean | SD | CV |
| C | Total (µg/ml) | 4.1 | 4.3 | 5.5 | 4.63 | 0.76 | 16.3% |
|  | Free (%) | <20.0 | <20.0 | <20.0 | — | — | — |
| W | Total (µg/ml) | 4.7 | 4.4 | 5.2 | 4.77 | 0.40 | 8.5% |
|  | Free (%) | <21.2 | <21.2 | <21.2 | — | — | — |
| Y | Total (µg/ml) | 5.8 | 6.2 | 6.5 | 6.17 | 0.35 | 5.7% |
|  | Free (%) | <21.2 | <21.2 | <21.2 | — | — | — |

It will be understood that the invention has been described by way of example only and modifications may be made whilst remaining within the scope and spirit of the invention.

REFERENCES

The Contents of Which are Hereby Incorporated by Reference

[1] *Vaccines* (eds. Plotkin et al.) 4th edition, ISBN: 0721696880.
[2] Baker et al. (2003) *J Infect Dis* 188:66-73.
[3] Theilacker et al. (2003) *Infect Immun* 71:3875-84.
[4] Anonymous (2003) *Drugs R D* 4:383-5.
[5] Jones (2001) *Curr Opin Investig Drugs* 2:47-49.
[6] WO02/058737.
[7] WO03/007985.
[8] Rennels et al. (2002) *Pediatr Infect Dis J* 21:978-979.
[9] Campbell et al. (2002) *J Infect Dis* 186:1848-1851.
[10] Costantino et al. (1992) *Vaccine* 10:691-698.
[11] Lieberman et al. (1996) *JAMA* 275:1499-1503.
[12] Darkes & Plosker (2002) *Paediatr Drugs* 4:609-630.
[13] Ugozzoli (2002) *J Infect Dis* 186:1358-61.

[14] Granoff et al. (1997) *Infect Immun* 65:1710-5.
[15] Paradiso & Lindberg (1996) *Dev Biol Stand* 87:269-275.
[16] Corbel (1996) *Dev Biol Stand* 87:113-124.
[17] WO03/080678.
[18] Klug (1996) *Dev Biol Stand* 87:263-267.
[19] Plumb & Yost (1996) *Vaccine* 14:399-404.
[20] Tsai et al. (1994) *Vaccine* 12:700-706.
[21] Ricci et al. (2001) *Vaccine* 19:1989-1997.
[22] Yasuno et al. (1999) *Biosci Biotechnol Biochem* 63:1353-1359.
[23] Glode et al. (1979) *J Infect Dis* 139:52-56
[24] WO94/05325; U.S. Pat. No. 5,425,946.
[25] United Kingdom patent application 0323103.2
[26] Ravenscroft et al. (1999) *Vaccine* 17:2802-2816.
[27] Jumel et al. (2002) *Biotechnol Appl Biochem* 36:219-226.
[28] Hardy et al. (1988) *Anal Biochem* 170:54-62.
[29] Wang et al. (1990) *Anal Biochem* 190:182-187.
[30] Ramsay et al. (2001) *Lancet* 357(9251):195-196.
[31] Lindberg (1999) *Vaccine* 17 Suppl 2:S28-36.
[32] Buttery & Moxon (2000) *J R Coll Physicians Lond* 34:163-168.
[33] Ahmad & Chapnick (1999) *Infect Dis Clin North Am* 13:113-133, vii.
[34] Goldblatt (1998) *J. Med. Microbiol.* 47:563-567.
[35] European patent 0477508.
[36] U.S. Pat. No. 5,306,492.
[37] WO98/42721.
[38] *Conjugate Vaccines* (eds. Cruse et al.) ISBN 3805549326, particularly vol. 10:48-114.
[39] Hermanson (1996) *Bioconjugate Techniques* ISBN: 0123423368 or 012342335X.
[40] U.S. Pat. No. 4,761,283
[41] U.S. Pat. No. 4,356,170
[42] WO00/10599
[43] Gever et al. Med. Microbiol. Immunol, 165: 171-288 (1979).
[44] U.S. Pat. No. 4,057,685.
[45] U.S. Pat. Nos. 4,673,574; 4,761,283; 4,808,700.
[46] U.S. Pat. No. 4,459,286.
[47] U.S. Pat. No. 4,965,338
[48] U.S. Pat. No. 4,663,160.
[49] Anonymous (January 2002) *Research Disclosure*, 453077.
[50] Anderson (1983) *Infect Immun* 39(1):233-238.
[51] Anderson et al. (1985) *J Clin Invest* 76(1):52-59.
[52] EP-A-0372501.
[53] EP-A-0378881.
[54] EP-A-0427347.
[55] WO93/17712
[56] WO94/03208.
[57] WO98/58668.
[58] EP-A-0471177.
[59] WO91/01146
[60] Falugi et al. (2001) *Eur J Immunol* 31:3816-3824.
[61] EP-A-0594610.
[62] WO00/56360.
[63] WO02/091998.
[64] WO01/72337
[65] WO00/61761.
[66] WO99/42130
[67] WO96/40242
[68] Lawrence et al. (2000) *J Biol Chem* 23:17869-17877.
[69] Paoletti et al. (2001) *Vaccine* 19:2118-2126.
[70] WO00/56365.
[71] WO99/47174.
[72] Yurewicz et al. (1971) *J Biol Chem* 246:5596-5606.
[73] Bardotti et al (2000) *Vaccine* 18:1982-1993.
[74] WO02/09643.
[75] Katial et al. (2002) *Infect Immun* 70:702-707.
[76] WO01/52885.
[77] European patent 0301992.
[78] Bjune et al. (1991) *Lancet* 338(8775):1093-1096.
[79] Fukasawa et al. (1999) *Vaccine* 17:2951-2958.
[80] WO02/09746.
[81] Rosenqvist et al. (1998) *Dev. Biol. Stand* 92:323-333.
[82] Watson (2000) *Pediatr Infect Dis J* 19:331-332.
[83] Rubin (2000) *Pediatr Clin North Am* 47:269-285, v.
[84] Jedrzejas (2001) *Microbiol Mol Biol Rev* 65:187-207.
[85] Bell (2000) *Pediatr Infect Dis J* 19:1187-1188.
[86] Iwarson (1995) *APMIS* 103:321-326.
[87] Gerlich et al. (1990) *Vaccine* 8 Suppl:S63-68 & 79-80.
[88] Gustafsson et al. (1996) *N. Engl. J. Med.* 334:349-355.
[89] Rappuoli et al. (1991) *TIBTECH* 9:232-238.
[90] Del Guidice et al. (1998) *Molecular Aspects of Medicine* 19:1-70.
[91] Sutter et al. (2000) *Pediatr Clin North Am* 47:287-308.
[92] Zimmerman & Spann (1999) *Am Fam Physician* 59:113-118, 125-126.

The invention claimed is:

1. A process for analysing the saccharide content of a composition, wherein:
   (a) the composition comprises a capsular saccharide from serogroup C of *Neisseria meningitidis* and one or both of: (i) a capsular saccharide from serogroup W135 of *Neisseria meningitidis*; and/or (ii) a capsular saccharide from serogroup Y of *Neisseria Meningitidis*;
   (b) the process comprises a step of analysing the sialic acid content of the composition, and:
   (i) if the composition includes a serogroup W135 saccharide, a step of analysing the galactose content of the composition; (ii) if the composition includes a serogroup Y saccharide, a step of analysing the glucose content of the composition;
   (c) if the composition includes a serogroup W135 saccharide, the content of serogroup W135 saccharide in the composition is determined according to the results of the galactose analysis from step (b);
   (d) if the composition includes a serogroup Y saccharide, the content of serogroup Y saccharide in the composition is determined according to the results of the glucose analysis from step (b); and
   (e) the content of serogroup C saccharide in the composition is accurately determined by: (i) if the composition includes a serogroup W135 saccharide but not a serogroup Y saccharide, subtracting the galactose content of the composition from step (b) from the sialic acid content of the composition from step (b), to determine the content of serogroup C saccharide in the composition; (ii) if the composition includes a serogroup Y saccharide but not a serogroup W135 saccharide, subtracting the glucose content of the composition from step (b) from the sialic acid content of the composition from step (b), to determine the content of serogroup C saccharide in the composition; or (iii) if the composition includes both a serogroup W135 saccharide and a serogroup Y saccharide, subtracting the combined glucose and galactose content of the composition from step (b) from the sialic acid content of the composition from step (b), to determine the content of serogroup C saccharide in the composition.

2. The process of claim 1, wherein the composition comprises capsular saccharide from all three of serogroups C, W135 and Y of *Neisseria meningitides*.

3. The process of claim 2, wherein the composition comprises one or more further capsular saccharide(s).

4. The process of claim 3, wherein the one or more further capsular saccharide(s) is/are selected from the group consisting of: a capsular saccharide from serogroup A of N. meningitidis; and a capsular saccharide from *Haemophilus influenzae* b.

5. The process of claim 1, including a step of treating the composition in order to depolymerise the capsular saccharides to give their constituent monosaccharides.

6. The process of claim 1, wherein sialic acid content, glucose content and/or galactose content are measured by high performance anion exchange chromatography, optionally with pulsed amperometric detection.

7. The process of claim 1, wherein the process also includes step(s) in which one of more of the following components or properties is/are analysed: osmolality, pH, degree of polymerisation for individual saccharides or conjugates, protein content, aluminium content, detergent content, and preservative content.

8. The process of claim 1, wherein the capsular saccharides are derived from a saccharide-protein conjugate.

9. The process of claim 8, wherein the protein in the conjugate is a bacterial toxin or toxoid.

10. The process of claim 9, wherein the toxin or toxoid is selected from the group consisting of: diphtheria toxoid; tetanus toxoid; the CRM197 diphtheria toxin derivative; and protein D from *H. influenzae*.

11. A process for analysing a composition, wherein:
(a) the composition comprises a conjugate of a capsular saccharide from serogroup C of *Neisseria meningitidis* and one or both of: (i) a conjugate of a capsular saccharide from serogroup W135 of *Neisseria meningitidis*; and/or (ii) a conjugate of a capsular saccharide from serogroup Y of *Neisseria meningitidis;*
(b) the composition may comprise the capsular saccharides in unconjugated form;
(c) the content of any unconjugated capsular saccharides is determined by the process of any one of claims 1 to 7;
(d) the content of conjugated capsular saccharides is determined by the process of any one of claims 1 to 7; and, optionally,
(e) the ratio of conjugated:unconjugated saccharide in the composition is calculated for one or more of the capsular saccharides.

12. A method for releasing a vaccine for use by physicians, comprising the steps of: (a) manufacturing a vaccine containing a conjugate of a capsular saccharide from serogroup C of *Neisseria meningitidis* and one or both of: (i) a conjugate of a capsular saccharide from serogroup W135 of *Neisseria meningitidis*; and/or (ii) a conjugate of a capsular saccharide from serogroup Y of *Neisseria meningitidis*; (b) analysing the amount of conjugated and/or unconjugated saccharide in the vaccine for each of said capsular saccharides, according to the process of claim 1; and, if the results from step (b) indicate a saccharide content acceptable for clinical use, (c) releasing the vaccine for use by physicians.

13. A computer apparatus, comprising a non-transitory computer-readable storage medium storing computer-executable instructions for performing the process steps of any one of claims 1 to 11.

14. A non-transitory computer-readable storage medium storing computer-executable instructions for analysing the saccharide content of a composition, comprising computer-executable instructions for: (a) receiving data on the sialic acid content, and on the glucose and/or galactose content, of a sample; and (b) calculating from those data the saccharide content in the composition from serogroup C and from serogroup W135 and/or Y according to the process of any one of claims 1 to 11.

15. The process of claim 2, including a step of treating the composition in order to depolymerise the capsular saccharides to give their constituent monosaccharides.

16. The process of claim 3, including a step of treating the composition in order to depolymerise the capsular saccharides to give their constituent monosaccharides.

17. The process of claim 4, including a step of treating the composition in order to depolymerise the capsular saccharides to give their constituent monosaccharides.

* * * * *